United States Patent [19]

Chang et al.

[11] Patent Number: 5,571,768
[45] Date of Patent: *Nov. 5, 1996

[54] ZEOLITE FUNCTIONALIZED WITH ORGANOSILICEOUS GROUPS

[75] Inventors: Clarence D. Chang, Princeton; Paul G. Rodewald, Rocky Hill, both of N.J.

[73] Assignee: Mobil Oil Corporation, Fairfax, Va.

[*] Notice: The term of this patent shall not extend beyond the expiration date of Pat. No. 5,516,736.

[21] Appl. No.: 306,567

[22] Filed: Sep. 15, 1994

Related U.S. Application Data

[63] Continuation-in-part of Ser. No. 223,383, Apr. 5, 1994, Pat. No. 5,475,179, which is a continuation of Ser. No. 24,972, Mar. 2, 1993, abandoned, which is a continuation-in-part of Ser. No. 850,105, Mar. 12, 1992, which is a continuation-in-part of Ser. No. 38,310, Mar. 29, 1993, which is a continuation-in-part of Ser. No. 850,104, Mar. 12, 1992, abandoned.

[51] Int. Cl.$^6$ .............................. B01J 29/26; B01J 29/40
[52] U.S. Cl. ................... 502/64; 502/71; 502/85
[58] Field of Search ....................... 502/85, 64, 71

[56] References Cited

U.S. PATENT DOCUMENTS

| | | | |
|---|---|---|---|
| 3,682,996 | 8/1972 | Kerr | 260/448 C |
| 3,698,157 | 10/1972 | Allen et al. | 55/67 |
| 4,090,981 | 5/1978 | Rodewald | 252/455 Z |
| 4,100,215 | 7/1978 | Chen | 260/671 M |
| 4,127,616 | 11/1978 | Rodewald | 260/671 R |
| 4,477,583 | 10/1984 | Rodewald | 502/71 |
| 4,950,835 | 8/1990 | Wang et al. | 585/467 |
| 5,329,059 | 7/1994 | Marler | 585/475 |
| 5,367,099 | 11/1994 | Beck et al. | 502/85 |
| 5,371,312 | 12/1994 | Lago et al. | 585/733 |
| 5,406,015 | 4/1995 | Beck et al. | 585/475 |

FOREIGN PATENT DOCUMENTS

| | | |
|---|---|---|
| WO93/17987 | 9/1993 | WIPO . |
| WO93/17788 | 9/1993 | WIPO . |

OTHER PUBLICATIONS

Chamoumi et al. "Characterization of Offretite Modified by Silanation with Tetramethoxysilane and Octamethylcyclotetrasiloxane", *Zeolites*, vol. 14, Apr./May 1994, pp. 282–289.

*Primary Examiner*—Glenn A. Caldarola
*Attorney, Agent, or Firm*—R. A. Bleeker; P. W. Roberts

[57] ABSTRACT

There is provided a zeolite, such as ZSM-5, which is functionalized with at least one organosiliceous group of the formula, $SiR_n(OX)_{4-n}$, where R is at least one hydrocarbyl group, n is 1 or 2 and X is Si or H. There is also provided a method for functionalizing a zeolite by treatment with a silicone compound, such as hexamethyldisiloxane, under vapor phase conditions. This contacting may take place in the presence of hydrogen and an organic carrier. The functionalized zeolites may provide a catalyst which is both highly active and highly selective for converting aromatic hydrocarbons, especially alkylbenzene compounds, to products comprising the para-isomer of dialkylbenzenes. The disproportionation of toluene is an example of such a reaction.

40 Claims, 2 Drawing Sheets

ZEOLITE FUNCTIONALIZED WITH ORGANOSILICEOUS GROUPS

CROSS-REFERENCE TO RELATED APPLICATIONS

This application is a continuation-in-part of U.S. application Ser. No. 08/223,383, filed Apr. 5, 1994, now U.S. Pat. No. 5,475,179 which is a continuation of U.S. application Ser. No. 08/024,972, filed Mar. 2, 1993, now abandoned, which is a continuation-in-part of U.S. application Ser. No. 07/850,105, filed Mar. 12, 1992, which is also a continuation-in-part of copending U.S. application Ser. No. 08/038,310, filed Mar. 29, 1993, which is a continuation-in-part of U.S. application Ser. No. 07/850,104, filed Mar. 12, 1992, abandoned.

BACKGROUND

There is provided a zeolite which is functionalized with organosiliceous groups. There is also provided a method for making this zeolite by contacting the zeolite with a silicone compound having at least two silicon atoms.

alkyl-substituted benzene disproportionation to para-dialkyl-substituted benzene.

A representative para-dialkyl-substituted benzene is para-xylene. The production of para-xylene may be performed by methylation of toluene or by toluene disproportionation over a catalyst under conversion conditions. Examples include the reaction of toluene with methanol, as described by Chen et al., *J. Amer. Chem. Soc.*, 101, 6783 (1979), and toluene disproportionation, as described by Pines in *The Chemistry of Catalytic Hydrocarbon Conversions*, Academic Press, 72 (1981). Such methods may result in the production of a mixture of the three xylene isomers, i.e., para-xylene, ortho-xylene, and meta-xylene. Depending upon the degree of selectivity of the catalyst for para-xylene (para-selectivity) and the reaction conditions, different percentages of para-xylene are obtained. The yield, i.e., the amount of xylene produced as a proportion of the feedstock, is also affected by the catalyst and the reaction conditions.

The equilibrium reaction for the conversion of toluene to xylene and benzene proceeds as follows:

Shape-selective catalysis is described, e.g., by N. Y. Chen, W. E. Garwood, and F. G. Dwyer, *Shape Selective Catalysis in Industrial application*, 36, Marcel Dekker, Inc. (1989). Within a zeolite pore, hydrocarbon conversion reactions such as isomerization, disproportionation, alkylation, and transalkylation of aromatics are governed by constraints imposed by the channel size. Reactant selectivity may occur when a fraction of the feedstock is too large to enter the zeolite pores to react, while product selectivity may occur when some of the products cannot leave the zeolite channels. Product distributions can also be altered by transition state selectivity in which certain reactions cannot occur because the reaction transition state is too large to form within the zeolite pores or cages. Another type of selectivity results from configurational constraints on diffusion where the dimensions of the molecule approach that of the zeolite pore system. A small change in the dimensions of the molecule or the zeolite pore can result in large diffusion changes leading to different product distributions. This type of shape-selective catalysis is demonstrated, for example, in selective Various methods are known in the art for increasing the para-selectivity of zeolite catalysts. One such method is to modify the catalyst by treatment with a "selectivating agent." For example, U.S. Pat. Nos. 5,173,461; 4,950,835; 4,927,979; 4,465,886; 4,477,583; 4,379,761; 4,145,315; 4,127,616; 4,100,215; 4,090,981; 4,060,568; and 3,698,157 disclose specific methods for contacting a catalyst with a selectivating agent containing silicon ("silicon compound").

U.S. Pat. No. 4,548,914 describes another modification method involving impregnating catalysts with oxides that are difficult to reduce, such as those of magnesium, calcium, and/or phosphorus, followed by treatment with water vapor to improve para-selectivity.

European Patent No. 296,582 describes the modification of aluminosilicate catalysts by impregnating such catalysts with phosphorus-containing compounds and further modifying these catalysts by incorporating metals such as manganese, cobalt, silicon and Group IIA elements. The patent also describes the modification of zeolites with silicon compounds.

Traditionally, ex situ pre-selectivation of zeolites has involved single applications of the modifying compound. It may be noted, however, that the suggestion of multiple treatments was made in U.S. Pat. No. 4,283,306 to Herkes. The Herkes patent discloses the promotion of crystalline silica catalyst by application of an amorphous silica such as ethylorthosilicate (i.e., tetraethylorthosilicate). The Herkes patent contrasts the performance of catalyst treated once with an ethylorthosilicate solution followed by calcination against the performance of catalyst treated twice with ethylorthosilicate and calcined after each treatment. The Herkes disclosure shows that the twice-treated catalyst is less active and less selective than the once-treated catalyst as measured by methylation of toluene by methanol, indicating that the multiple ex situ selectivation confers no benefit and in fact reduces a catalyst's efficacy in shape-selective reactions.

Steaming has also been used in the preparation of zeolite catalysts to modify the alpha or improve stability. For example, U.S. Pat. No. 4,559,314 describes steaming a zeolite/binder composite at 200°–500° C. for at least an hour to enhance activity by raising the alpha. U.S. Pat. No. 4,522,929 describes pre-steaming a fresh zeolite catalyst so that the alpha activity first rises then falls to the level of the fresh unsteamed catalyst, producing a stable catalyst which may be used in xylene isomerization. U.S. Pat. No. 4,443,554 describes steaming inactive zeolites (Na ZSM-5) to increase alpha activity. U.S. Pat. No. 4,487,843 describes contacting a zeolite with steam prior to loading with a Group IIIB metal.

Various organic compounds have been employed as carriers for silicon compounds in the silicon impregnation methods applied to zeolite catalysts. For example, U.S. Pat. Nos. 4,145,315; 4,127,616; 4,090,981; and 4,060,568 describe the use of inter alia $C_{5-7}$ alkanes as solvents for silicon impregnation.

SUMMARY

There is provided a zeolite functionalized with at least one organosiliceous group of the formula, $SiR_n(OX)_{4-n}$, where R is at least one hydrocarbyl group, n is 1 or 2 and X is Si or H.

There is also provided a method for selectivating a zeolite, said method comprising reacting said zeolite with a silicone compound under vapor phase conditions, said silicone compound having at least two silicon atoms, the silicon atoms being connected to one another through oxygen atoms, the remainder of the bonds extending from the silicon atoms being connected to hydrocarbyl groups having from 1 to 10 carbon atoms.

There are also provided hydrocarbon conversion processes using the present functionalized zeolite as a catalyst.

EMBODIMENTS

The parent zeolite, which is subjected to the functionalization or selectivation treatment described herein, is preferably an intermediate pore size zeolite. Such intermediate pore size zeolites may have a Constraint Index of between about 1 and 12. A method for determining Constraint Index is described in U.S. Pat. No. 4,016,218. Examples of zeolites which have a Constraint Index from about 1 to 12 include ZSM-5, ZSM-11, ZSM-12, ZSM-22, ZSM-23, ZSM-35, ZSM-48, ZSM-50 and ZSM-57. An especially preferred zeolite is ZSM-5. Such zeolites are described, for example, in U.S. Pat. Nos. 3,702,886; Re. 29,949; 3,709,979; 3,832,449; 4,046,859; 4,556,447; 4,076,842; 4,016,245; 4,397,827; 4,640,849; 4,046,685; 4,175,114; 4,199,556; 4,341,7448; 3,308,069; and Re. No. 28,341.

The present zeolite may be combined with a binder material for the zeolite. This binder material is preferably an inert, non-alumina binder material, such as a silica binder. The zeolite may be subjected to one or more selectivation treatments after the zeolite is combined with the binder material. Optionally, however, the zeolite may be selectivated in the unbound state.

Procedures for preparing silica bound zeolites, such as ZSM-5, are described in U.S. Pat. Nos. 4,582,815; 5,053,374; and 5,182,242. A particular procedure for binding ZSM-5 with a silica binder involves an extrusion process.

A particular process for preparing silica bound ZSM-5 may comprise the steps of:

(a) mulling and then extruding a mixture comprising water, ZSM-5, colloidal silica and sodium ions under conditions sufficient to form an extrudate having an intermediate green strength sufficient to resist attrition during ion exchange step (b) set forth hereinafter;

(b) contacting the uncalcined extrudate of step (a) with an aqueous solution comprising ammonium cations under conditions sufficient to exchange cations in said ZSM-5 with ammonium cations; and (c) calcining the ammonium exchanged extrudate of step (b) under conditions sufficient to generate the hydrogen form of said ZSM-5 and increase the crush strength of said extrudate.

The silicone compound which may be used to functionalize the present zeolite may be considered to be constructed of a siloxy backbone structure capped with terminal hydrocarbyl groups. This siloxy backbone structure may be a chain structure represented by the formula where p is from 1 to 9. This siloxy backbone structure may also be a cyclic structure represented by the formula where q is from 2 to 10. Branched chain structures and composite chain/cyclic structures are also possible for the siloxy backbone of the silicone functionalizing agent.

The hydrocarbyl groups which cap the available bonds of the siloxy backbone may have from 1 to 10 carbon atoms. Examples of such hydrocarbyl groups are methyl and phenyl.

Examples of silicone compounds having a chain siloxy backbone structure include those of the formula where $R_1$, $R_2$, $R_3$, $R_4$, $R_5$, and $R_6$ are independently methyl or phenyl and m is from 1 to 10, e.g., from 1 to 4. Preferably, no more than one phenyl group is bonded to each silicon atom. Particular examples of such silicone compounds having a chain siloxy backbone structure include hexamethyldisiloxane, decamethyltetrasiloxane and diphenyltetramethyldisiloxane. Particular examples of silicone compounds having a cyclic siloxy backbone structure include octamethylcyclotetrasiloxane and decamethylcyclopentasiloxane.

As discussed more fully hereinafter, the present treatment, which results in the generation of the present functionalized zeolites, also serves to selectivate the zeolite for catalyzing certain reactions such as the disproportionation of toluene. Accordingly, the present functionalization treatment is also referred to herein as a selectivation treatment.

The present zeolite may be selectivated by more than one selectivation method, including those which are distinguished from the present selectivation method. In particular, prior to contact with the present silicone functionalizing agent, the zeolite may be contacted with an organosilicon compound, followed by calcination in an oxygen containing atmosphere. Such a pretreatment of the zeolite is referred to herein as a preselectivation treatment.

In accordance with an example of a preselectivation method, the catalyst is preselectivated by single or multiple treatments with a liquid organosilicon compound in a liquid carrier, each treatment being followed by calcination of the treated material in an oxygen containing atmosphere, e.g., air.

In accordance with the multiple impregnation preselectivation method, the zeolite is treated at least twice, e.g., at least 3 times, e.g., from 4 to 6 times, with a liquid medium comprising a liquid carrier and at least one liquid organosilicon compound. The organosilicon compound may be present in the form of a solute dissolved in the liquid carrier or in the form of emulsified droplets in the liquid carrier. For the purposes of the present disclosure, it will be understood that a normally solid organosilicon compound will be considered to be a liquid (i.e., in the liquid state) when it is dissolved or emulsified in a liquid medium. The liquid carrier may be water, an organic liquid or a combination of water and an organic liquid. Particularly when the liquid medium comprises an emulsion of the organosilicon compound in water, the liquid medium may also comprise an emulsifying agent, such as a surfactant.

The organosilicon compound preselectivating agent may be, for example, a silicone, a siloxane, a silane or mixtures thereof. These organosilicon compounds may have at least 2 silicon atoms per molecule. These organosilicon compounds may be solids in pure form, provided that they are soluble or otherwise convertible to the liquid form upon combination with the liquid carrier medium. The molecular weight of the silicone, siloxane or silane compound employed as a preselectivating agent may be between about 80 and about 20,000, and preferably within the approximate range of 150 to 10,000. Representative preselectivation silicone compounds include dimethyl silicone, diethyl silicone, phenylmethyl silicone, methylhydrogen silicone, ethylhydrogen silicone, phenylhydrogen silicone, methylethyl silicone, phenylethylsilicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone, and ethylvinyl silicone. The preselectivating silicone, siloxane or silane compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used as preselectivating agents, as may silicones with other functional groups.

Preferred organosilicon preselectivating agents, particularly when the preselectivating agent is dissolved in an organic carrier or emulsified in an aqueous carrier, include dimethylphenyl methyl polysiloxane (e.g., Dow-550) and phenylmethyl polysiloxane (e.g., Dow-710). Dow-550 and Dow-710 are available from Dow Chemical Co., Midland, Mich.

When the organosilicon preselectivating agent is present in the form of a water soluble compound in an aqueous solution, the organosilicon may be substituted with one or more hydrophilic functional groups or moieties, which serve to promote the overall water solubility of the organosilicon compound. These hydrophilic functional groups may include one — or more organoamine groups, such as —N(CH$_3$)$_3$, —N(C$_2$H$_5$)$_3$ and N(C$_3$H$_7$)$_3$. A preferred water soluble organosilicon preselectivating agent is an n-propylamine silane, available as Hydrosil 2627 from Huls America.

When the zeolite is preselectivated by a single or multiple impregnation technique, the zeolite is calcined after each impregnation to remove the carrier and to convert the liquid organosilicon compound to a solid residue material thereof. This solid residue material is referred to herein as a siliceous solid material, insofar as this material is believed to be a polymeric species having a high content of silicon atoms in the various structures thereof. However, this siliceous solid residue material may also comprise carbon atoms in the structure thereof, resulting from the residue of the organo portion of the organosilicon compound used to impregnate the catalyst.

Following each impregnation, the zeolite may be calcined at a rate of from about 0.2° C./minute to about 5° C./minute to a temperature greater than 200°0 C., but below the temperature at which the crystallinity of the zeolite is adversely affected. This calcination temperature may be below 600° C., e.g., within the approximate range of 350° C. to 550° C. The duration of calcination at the calcination temperature may be from 1 to 24 hours, e.g., from 2 to 6 hours.

The impregnated zeolite may be calcined in an inert or oxidizing atmosphere. An example of such an inert atmosphere is a nitrogen, i.e., N$_2$, atmosphere. An example of an oxidizing atmosphere is an oxygen containing atmosphere, such as air. Calcination may take place initially in an inert, e.g., $N_2$, atmosphere, followed by calcination in an oxygen containing atmosphere, such as air or a mixture of air and $N_2$. Calcination should be performed in an atmosphere substantially free of water vapor to avoid undesirable uncontrolled steaming of the zeolite. The zeolite may be calcined once or more than once following each impregnation. The various calcinations following each impregnation need not be identical, but may vary with respect to the temperature, the rate of temperature rise, the atmosphere and the duration of calcination.

The amount of siliceous residue material which is deposited on the zeolite or bound zeolite is dependent upon a number of factors including the temperatures of the impregnation and calcination steps, the concentration of the organosilicon compound in the carrying medium, the degree to which the catalyst has been dried prior to contact with the organosilicon compound, the atmosphere used in the calcination and duration of the calcination.

Preferably, the kinetic diameter of both the organosilicon compound, which is used to preselectivate the zeolite, and the silicone compound, which is used to functionalize the zeolite, is larger than the zeolite pore diameter, in order to avoid entry of the organosilicon or silicone compound into the zeolite pores and any concomitant reduction in the internal activity of the zeolite.

In accordance with the present selectivation or functionalization method described herein, the zeolite is contacted with a feed stream comprising a silicone compound under vapor phase conditions. The silicone compound may be applied to the zeolite neat (i.e., in the absence of a carrier or other cofeed) by a chemical vapor deposition technique. This feed stream may also comprise hydrogen and/or an organic carrier. Vapor phase conditions may include a temperature ranging from about 100° C. to about 600° C., e.g., from about 300° C. to about 500° C. When the silicone compound is applied neat, reduced pressures, e.g., from about 0.5 Torr to less than atmospheric, may be used. Preferably, however, the silicone compound is applied along with cofed hydrogen (i.e., $H_2$) and an organic carrier. In general, vapor phase conditions may include a pressure ranging from about 0 to about 2000 psig, e.g., from about 15 to about 800 psig, a mole ratio of hydrogen to hydrocarbons (e.g., toluene) from about 0.1 to 20, e.g., from about 0.1 to 10, e.g., from about 1 to about 4, and a weight hourly space velocity (WHSV) from about 0.1 to about 100 $hr^{-1}$, e.g., from about 0.1 to about 10 $hr^{-1}$. The organic carrier may be a hydrocarbon, especially an aromatic hydrocarbon such as toluene, benzene, xylenes and trimethylbenzenes. Toluene may comprise about 50 wt % to 100 wt %, e.g., at least 80 wt %, of the hydrocarbons in the feedstock.

When a reactive hydrocarbon, such as toluene is included in the feedstock, the presence of a sufficient amount of hydrogen in the selectivation feedstock is necessary to prevent rapid aging of the catalyst during the selectivation process resulting in an excessive reduction in the zeolite activity, possibly accompanied by a reduction in toluene disproportionation selectivity to para-xylene. This rapid aging is believed to result from a rapid build-up of excessive amounts of carbonaceous deposits (i.e., coke), which may even extend into the pore system of the zeolite in the catalyst. However, even when hydrogen is used in optimal fashion to prevent aging during the selectivation process, a small amount of carbonaceous deposit may form on the catalyst. The presence of hydrogen may also serve to induce or enhance the chemical reaction between the zeolite and the selectivating agent, which results in the functionalization of the zeolite. This chemical reaction is also believed to be induced or enhanced by the elevated contact temperatures, which are needed to maintain the silicone functionalizing agent in the vapor phase.

Confirmation of the reaction between the zeolite and the silicone compound may be made by an appropriate analysis of the zeolite after the reaction, as well as by monitoring and analyzing the off-gases produced by the reaction.

Figure 1A:
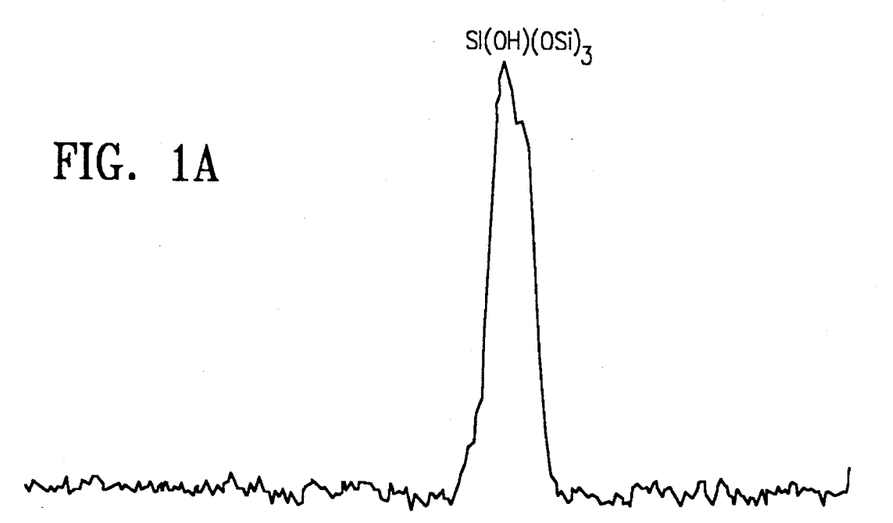
FIG. 1A is a Si NMR spectrum showing the presence of silanol groups of the formula, $Si(OH)(OSi)_3$, in a zeolite prior to functionalization using a silicone selectivating agent.
Figure 1B:
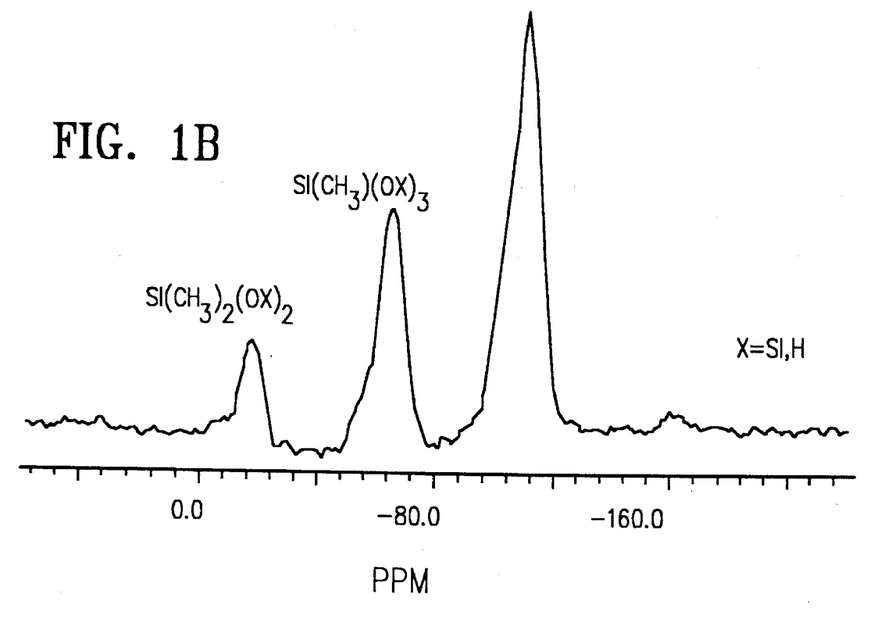
FIG. 1B is a Si NMR spectrum showing the substantial reduction of silanol groups of the formula, $Si(OH)(OSi)_3$, and the generation of organosiliceous groups of the formulae, $Si(CH_3)(OX)_3$ and $Si(CH_3)_2(OX)_2$, where X is Si or H, in a zeolite after functionalization using a silicone selectivating agent.

The amorphous silica-bound catalyst of this Example was analyzed by NMR both before and after selectivation. FIG. 1A shows the Si NMR spectrum with a strong silanol signal characteristic of a composite spectrum of ZSM-5 and amorphous silica. FIG. 1B shows the Si NMR of the catalyst after selectivation. The silanol signal has been greatly reduced indicative of reaction of the siloxane with surface silanols. The spectrum also shows two new signals corresponding to surface bonded methyl- and dimethylsilyl species.

Figure 2:
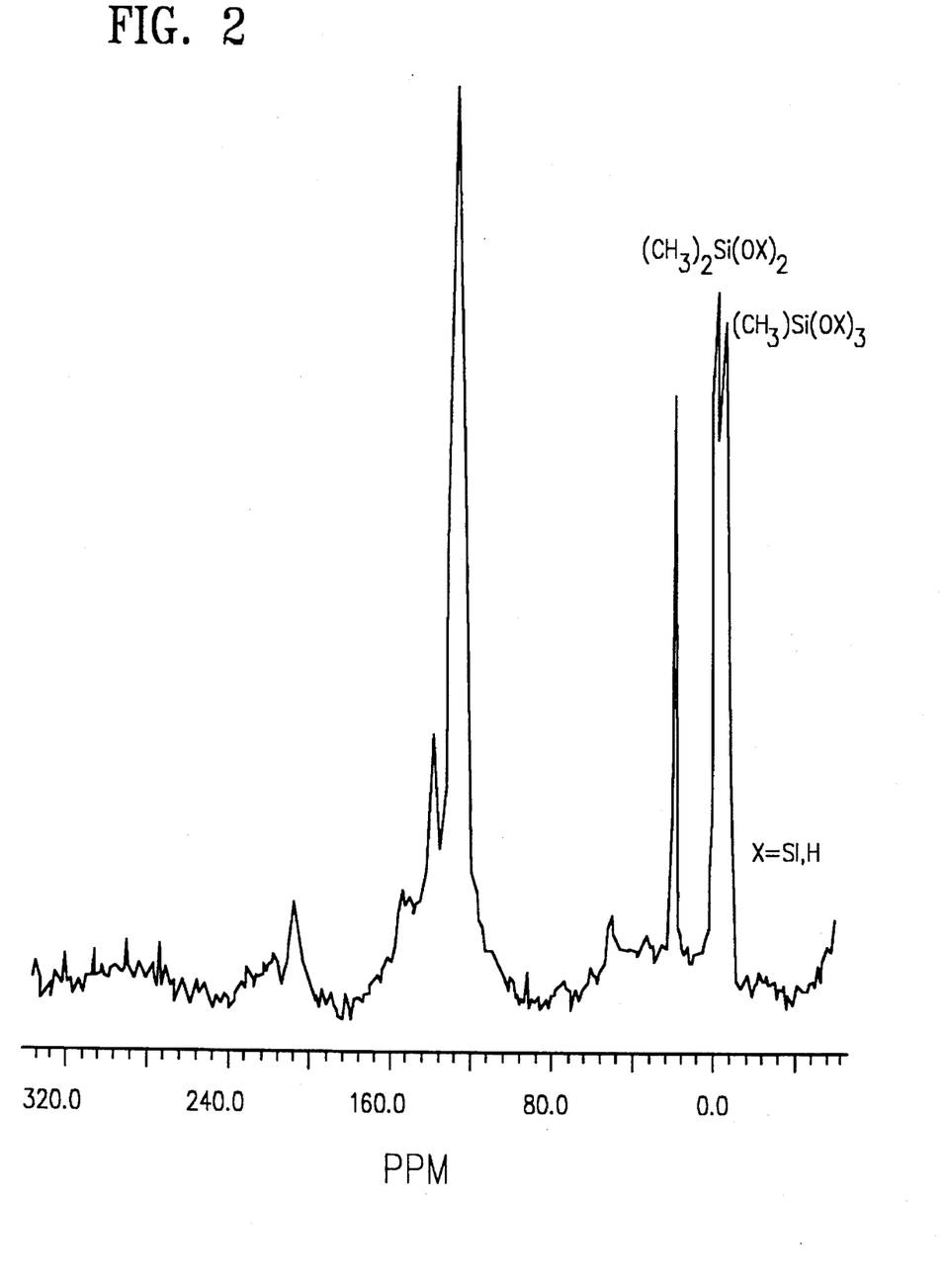
FIG. 2 is C NMR spectrum showing complementary evidence to that presented in FIG. 1B for the presence of at least two distinct organosiliceous groups of the formulae, $Si(CH_3)(OX)_3$ and $Si(CH_3)_2(OX)_2$, where X is Si or H, in a zeolite after functionalization using a silicone selectivating agent.

FIG. 2 shows the C NMR data for the selectivated catalyst and confirms the presence of the methyl- and dimethylsilyl surface species.

The present functionalized zeolite is a catalyst. This catalyst may be used alone or in combination with other catalyst components included in catalysts of this type. Such other components include binders and hydrogenation/dehydrogenation components. Accordingly, it will be understood that the term, present catalyst, as used herein is intended to connote the present functionalized zeolite in combination with other such catalyst components, if any.

The present zeolite may optionally be treated, before, during or after contact with the functionalizing agent, with selectivating agents containing atoms other than silicon or carbon. Such optional selectivation agents may include atoms such as P, Mg, B, N, Ce, Ca and Sr. However, insofar as the present catalyst may be free of treatment with such optional selectivation agents, the present catalyst may contain less than 500 ppm of each of the following elements as measured by elemental analysis: P, Mg, B, N, Ce, Ca, and Sr.

While not wishing to be bound by any theory, it is theorized that the extreme selectivity of the present catalyst is obtained by rendering acid sites on the external surfaces of the zeolite substantially inaccessible to reactants, while possibly increasing the tortuosity of the catalyst pore system. In a toluene disproportionation process using a non-selectivated catalyst, acid sites existing on the external surfaces of the zeolite are believed to isomerize the product para-xylene back to an equilibrium level with the other two xylene isomers, thereby reducing the amount of para-xylene in the xylenes to only about 24%. By reducing the availability of these external acid sites to the product para-xylene, it is theorized that a relatively high proportion of the para isomer can be retained. It is theorized that external zeolite acid sites are blocked or otherwise unavailable to para-xylene in the present catalyst. The extreme para-selectivity of the present catalyst is especially surprising in the highly active forms of the catalyst.

The "alpha value" of a catalyst is an approximate indication of its catalytic cracking activity. The alpha test is described in U. S. Pat. No. 3,354,078 and in the *Journal of Catalysis*, Vol. 4, 522–529 (1965); Vol. 6, 278 (1966); and Vol. 61, 395 (1980), each incorporated herein by reference to that description. It is noted that intrinsic rate constants for many acid-catalyzed reactions are proportional to the alpha value for a particular crystalline silicate catalyst (see "The Active Site of Acidic Aluminosilicate Catalysts," *Nature*, Vol. 309, No. 5959, 589–591, (1984). The experimental conditions of the alpha test preferably include a constant temperature of 538° C. and a variable flow rate as described in detail in the *Journal of Catalysis*, Vol. 61, 395 (1980). The present catalysts may have an alpha value greater than 50, e.g., greater than 200, e.g., from about 200 to about 500. The alpha value of the catalyst may be increased by initially treating the catalyst with organic or mineral acid, e.g., oxalic acid or nitric acid, or by mild steaming before selectivation. This type of steaming is discussed in U.S. Pat. No. 4,326, 994.

The silica to alumina ratio of zeolites may be determined by conventional analysis. This ratio is meant to represent, as closely as possible, the ratio in the rigid atomic framework of the zeolite crystal and to exclude silicon or aluminum in the binder or in cationic or other form within the channels. The silica to alumina molar ratio of the zeolites used to prepare the present catalysts may be less than 60, e.g., less than 40, e.g., from about 20 to about 40. It will be appreciated that it may be extremely difficult to directly measure the silica to alumina ratio of zeolite after it has been combined with a binder material and selectivated by methods described hereinabove. Accordingly, the silica to alumina ratio has been expressed hereinabove in term of the silica to alumina ratio of the parent zeolite, i.e., the zeolite used to prepare the catalyst, as measured prior the functionalization of the zeolite and prior to the combination of this zeolite with the other catalyst components.

The crystal size of the parent zeolites of the present catalysts is preferably greater than 0.1 microns, as calculated by methods described hereinbelow. The accurate direct measurement of the crystal size of zeolite materials is frequently very difficult. Microscopy methods, such as SEM and TEM, may be used, but these methods require measurements of a large number of crystals and, for each crystal measured, values may be evaluated in up to three dimensions. Furthermore, in order to more completely characterize the crystal size of a batch of crystals, one should calculate the average crystal size, as well as the degree of variance from this average in terms of a crystal size distribution. Rather than relying upon such complex evaluations, crystal size is expressed herein in terms of a calculated value of average crystal size obtained by measuring the rate of sorption of 2,2-dimethylbutane at 90° C. and 60 torr hydrocarbon pressure. The crystal size is computed by applying the diffusion equation given by J. Crank, *The Mathematics of Diffusion*, Clarendon Press, 52–56 (1957), for the rate of sorbate uptake by a solid whose diffusion properties can be approximated by a plane sheet model. In addition, the diffusion constant of 2,2-dimethylbutane, D, under these conditions, is taken to be $1.5 \times 10^{-14}$ cm$^2$/sec. The relation between crystal size measured in microns, d, and diffusion time measured in minutes, $t_{0.3}$, the time required for the uptake of 30% capacity of hydrocarbon, is:

$$d=0.0704 \times t_{0.3}^{1/2}.$$

Particular measurements expressed herein were made on a computer controlled, thermogravimetric electrobalance, but there are numerous ways one skilled in the art could obtain the data. Examples of larger crystal material described herein have a sorption time, $t_{0.3}$, of 497 minutes, which gives a calculated crystal size of 1.6 microns. Examples of smaller crystal material described herein have a sorption time of 7.8 minutes, and a calculated size of 0.20 microns.

As pointed out in the aforementioned U.S. Pat. No. 4,117,026, larger crystal size zeolites tend to have a greater intrinsic para-selectivity than smaller crystal size zeolites. It is theorized that this difference is attributable to the smaller ratio of external surface area to available internal surface area for larger zeolites as compared to smaller crystal size zeolites. Since it would theoretically require less selectivation to neutralize the external surface area of the more intrinsically para-selective larger crystal size zeolites, larger crystal size zeolites would be preferred to smaller crystal size zeolites, provided that all other factors were equal. However, there are other factors which tend to mitigate against a preference for larger crystal size zeolites, particularly ZSM-5. More particularly, larger crystal size ZSM-5 having a high activity and corresponding low silica to alumina molar ratio, e.g., from about 20 to about 40, is considerably more difficult to prepare than smaller crystal size ZSM-5, especially on a commercial scale. A particularly surprising aspect of the present catalysts is that the zeolites thereof may comprise relatively small crystal size ZSM-5, e.g., having a crystal size of from about 0.1 to about 0.5 microns and a silica to alumina molar ratio of from about 20 to 40, and still have an extremely high degree of para-selectivity. When larger crystal size ZSM-5 is chosen for the present catalyst, this the crystal size of this ZSM-5 may be, for example, from about 1 to 2 microns.

The present catalyst is particularly adapted for the production of para-xylene via the catalytic disproportionation of toluene. More particularly, this catalyst, under disproportionation conditions, is capable of high conversions of toluene, while at the same time producing a very high proportion of para-xylene among the total of the xylene isomers. However, it will be understood that this catalyst may also be used to catalyze other organic, especially hydrocarbon, conversion reactions.

When the present catalyst is used in a toluene disproportionation reaction, the reaction conditions may include a temperature of about 350° C.–540° C., a pressure of about atmospheric—5000 psig, a toluene feed rate of about 0.1–20 WHSV, and a hydrogen to toluene mole ratio of about 0.1–20. The hydrogen cofeed serves to suppress catalyst aging, thereby dramatically increasing the cycle length.

When the present catalyst is used in an ethylbenzene disproportionation reaction, the reaction conditions may include a temperature of about 200° C. to about 600° C., e.g., from about 350° C. to about 540° C.; a pressure of from about atmospheric to about 5000 psig, e.g., from about 100 to about 1000 psig; an ethylbenzene feed rate of from about 0.1 WHSV to about 20 WHSV, e.g., from about 2 WHSV to about 10 WHSV; and a hydrogen to ethylbenzene mole ratio of from about 0.1 to about 20, e.g., from about 2 to about 6.

The present catalysts may be used to convert paraffins from high to low molecular weight hydrocarbons in a dewaxing process. Examples of such dewaxing processes are disclosed in U. S. Pat. Nos. 3,700,585; Re. 28,398; 3,968,024; and 4,181,598, the entire disclosures of which are incorporated herein by reference. Hydrocarbon feeds for dewaxing processes include petroleum stocks which have a freeze point or pour point problem, e.g., petroleum stocks boiling above 350° F. Lubricating oil stocks may be feedstocks to a dewaxing process. The dewaxing may be carried out under either cracking or hydrocracking conditions. Cracking conditions for dewaxing may include a liquid hourly space velocity (LHSV) between about 0.5 and 200, a temperature between about 288° C. (550° F.) and 590° C. (1100° F.), a pressure between about subatmospheric and several hundred atmospheres. Hydrocracking conditions for dewaxing may include a liquid hourly space velocity (LHSV) between about 0.1 and 10, a temperature between about 340° C. (650° F.) and 538° C. (100° F.), a pressure between about 100 and 3000 psig, and a hydrogen to hydrocarbon mole ratio between about one and 20.

The present catalysts may be used to catalyze a variety of alkylaromatic conversion reactions, including isomerization reactions. Such conversions include those described, for example, in U.S. Pat. Nos. 3,856,872; 3,856,873; Re. 30,157; 4,101,595; 4,101,597; 4,312,790; Re. 31,919; and 4,224,141, the entire disclosures of which are incorporated by reference.

As per process conditions described in U.S. Pat. No. 3,856,872 to Morrison, the present catalyst may be used for catalyzing the conversion of $C_8$ aromatics, i.e., xylene and/or ethylbenzene, to para-xylene (octafining) at a temperature of 550° F. (288° C.) to 900° F. (482° C.), a pressure of 150 to 300 psig, and a liquid hourly space velocity (LHSV) of 1 to 200. When used in this reaction, the catalyst may comprise a hydrogenation metal, such as platinum or nickel, and the feed to the reaction may include hydrogen.

As per process conditions described in U.S. Pat. No. 3,856,873 to Burress, the present catalyst may be used for catalyzing the conversion of mixtures of $C_8$ aromatic hydrocarbons to para-xylene in a vapor phase reaction at a temperature of 500° F. (260° C.) to 1000° F. (538° C.), a pressure of 0 (atmospheric) to 1000 psig, and a weight hourly space velocity (WHSV) of 0.5 to 250 with no added hydrogen.

As per process conditions described in U.S. Pat. No. 4,476,330 to Kerr et al., the present catalyst may be used for catalyzing the conversion of aliphatic oxygenates to a higher molecular weight compound at a temperature of 70° F. (21° C.) to 1400° F. (760° C.). The feeds include lower aliphatic organic oxygenates having up to 6 carbon atoms. The oxygenates may be selected from the group consisting of acetals, ketals, acid halides, alcohols, carboxylic acids, aldehydes, acid anhydrides, epoxides, ethers, hemiacetals, gem diols, hydroxy acids, ketones, ketenes, lactones, peracids, peroxides and sugars, especially alcohols, ethers and esters.

The present catalysts may be used as catalysts in the oligomerization of olefins to form gasoline, distillate, lube oils and/or chemicals. Examples of such oligomerization processes are disclosed in U.S. Pat. Nos. 4,517,399; 4,520,221; 4,547,609; and 4,547,613, the entire disclosures of which are incorporated herein by reference.

As per process conditions described in U.S. Pat. No. 4,517,399 to Chester et al., the present catalyst may be used for catalyzing the conversion of olefins having from 3 to 18 carbon atoms, e.g., propylene, to high viscosity, low pour point lubricating oils. Conversion conditions may include a temperature of 350° F. (177° C.) to 650° F. (343° C.), a pressure of 100 to 5000 psig, and a weight hourly space velocity (WHSV) of 0.1 to 10.

The present catalysts may be used as catalysts in the conversion of a variety of aromatic compounds to provide dialkyl-benzene products which are highly enriched in the para-dialkyl substituted benzene isomer. Conversion reactions of this type include aromatics alkylation, transalkylation and disproportionation. Examples of such aromatic alkylation processes are disclosed in U.S. Pat. Nos. 3,755,483; 4,086,287; 4,117,024; and 4,117,026, the entire disclosures of which are incorporated herein by reference.

As per process conditions described in U.S. Pat. No. 3,755,483 to Burress, the present catalyst may be used for catalyzing the alkylation of aromatic hydrocarbons, such as benzene, naphthalene, anthracene and substituted derivatives thereof, e.g., toluene and xylene, with alkylating agents having 1 to 24 carbon atoms under vapor phase conditions. The alkylating agents may be selected from the group consisting of olefins, such as ethylene, propylene and dodecene, aldehydes, such as formaldehyde, alkyl halides and alcohols. Conversion conditions may include an inlet temperature of up to about 900° F. (428° C.), with a reactor bed temperature of up to about 1050° F. (566° C.), a pressure of about atmospheric to about 3000 psig, a ratio of aromatic/alkylating agent of about 1:1 to about 20:1 and a weight hourly space velocity (WHSV) of 20 to 3000.

As per process conditions described in U.S. Pat. No. 4,086,287 to Kaeding et al., the present catalyst may be used for catalyzing the ethylation of toluene or ethylbenzene to produce a para-ethyl derivative, e.g., para-ethyltoluene. Conversion conditions may include a temperature of from about 250° C. to about 600° C., a pressure of 0.1 atmospheres to about 100 atmospheres, a ratio of aromatic/ethylating agent of about 1:1 to about 10:1 and a weight hourly space velocity (WHSV) of 0.1 to 100.

The present catalysts may be used as catalysts in the conversion of light paraffins and olefins to aromatic compounds. Examples of such conversions are disclosed in U.S. Pat. Nos. 3,760,024 and 3,756,942, the entire disclosures of which are incorporated herein by reference.

As per process conditions described in U.S. Pat. No. 3,760,024 to Cattanach, the present catalyst may be used for catalyzing the conversion of paraffins having 2 to 4 carbon atoms and/or olefins to aromatics having from 6 to 10 carbon atoms. The catalyst may, optionally, include a hydrogenation/dehydrogenation component. Conversion conditions may include a temperature of from about 100° C. to about 650° C., a pressure of 0 to about 1000 psig, a ratio of hydrogen/hydrocarbon of about 0 to about 20 and a weight hourly space velocity (WHSV) of 0.1 to 500.

The present catalysts may be used as catalysts in the synthesis of pyridine and substituted pyridines. Process conditions may be selected from those disclosed in U.S. Pat. Nos. 4,675,410 and 4,220,783, the entire disclosures of which are incorporated herein by reference.

The present catalysts may be used as catalysts in the synthesis of caprolactam by the Beckmann rearrangement of cyclohexane oxime. Process conditions may be selected from those disclosed in U.S. Pat. No. 4,359,421, the entire disclosures of which are incorporated herein by reference.

Accordingly, it will be understood that the present catalysts may be used to catalyze a variety of organic, e.g., hydrocarbon, conversion processes. Examples of such processes include cracking hydrocarbons with reaction conditions including a temperature of from about 300° C. to about 700° C., a pressure of from about 0.1 atmosphere (bar) to about 30 atmospheres and a weight hourly space velocity of from about 0.1 $hr^{-1}$ to about 20 $hr^{-1}$; dehydrogenating hydrocarbon compounds with reaction conditions including a temperature of from about 300° C. to about 700° C., a pressure of from about 0.1 atmosphere to about 10 atmospheres and weight hourly space velocity of from about 0.1 to about 20; converting paraffins to aromatics with reaction conditions including a temperature of from about 300° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting olefins to aromatics, e.g., benzene, toluene and xylene, with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting alcohols, e.g., methanol, or ethers, e.g., dimethylether, or mixtures thereof to hydrocarbons including olefins and/or aromatics with reaction conditions including a temperature of from about 275° C. to about 600° C., a pressure of from about 0.5 atmosphere to about 50 atmospheres and a liquid hourly space velocity of from about 0.5 to about 100; isomerizing xylene feedstock components with reaction conditions including a temperature of from about 230° C. to about 510° C., a pressure of from about 3 atmospheres to about 35 atmospheres, a weight hourly space velocity of from about 0.1 to about 200 and a hydrogen/hydrocarbon mole ratio of from about 0 to about 100; disproportionating toluene with reaction conditions including a temperature of from about 200° C. to about 760° C., a pressure from about atmospheric to about 60 atmospheres and a weight hourly space velocity of from about 0.08 to about 20; alkylating aromatic hydrocarbons, e.g., benzene and alkylbenzenes in the presence of an alkylating agent, e.g., olefins, formaldehyde, alkyl halides and alcohols, with reaction conditions including a temperature of from about 250° C. to about 500° C., a pressure of from about atmospheric to about 200 atmospheres, a weight hourly space velocity of from about 2 to about 2000 and an aromatic hydrocarbon/alkylating agent mole ratio of from about 1/1 to about 20/1; and transalkylkating aromatic hydrocarbons in the presence of polyalkylaromatic hydrocarbons with reaction conditions including a temperature of from about 340° C. to about 500° C., a pressure of from about atmospheric to about 200 atmospheres, a weight hourly space velocity of from about 10 to about 1000 and an aromatic hydrocarbon/polyalkylaromatic hydrocarbon mole ratio of from about 1/1 to about 16/1.

In general, therefore, catalytic conversion conditions over the present catalyst may include a temperature of from about 100° C. to about 760° C., a pressure of from about 0.1 atmosphere (bar) to about 200 atmospheres (bar), a weight hourly space velocity of from about 0.08 $hr^{-1}$ to about 2000 $hr^{-1}$ and a hydrogen/organic, e.g., hydrocarbon compound, of from 0 to about 100.

Especially when the present catalyst is intended for use as a toluene disproportionation process, the binder for this catalyst is preferably an inert, non-alumina containing material, such as silica. However, the binder may also be selected from other materials which may be used exclusively or in combination with one another or with silica. Examples of such binder materials include alumina, zirconia, magnesia, titania, thoria and boria. These materials may be used in the form of dried inorganic oxide gels of gelatinous precipitates. Examples of clay binder materials include bentonite and kieselguhr. The relative proportion of zeolite to the binder material may be about 30 to about 90 percent by weight. The bound catalyst may be in the form of an extrudate, beads or fluidizable microspheres.

An optional component of the present catalyst is a hydrogenation/dehydrogenation component. Examples of such components include the oxide, hydroxide or free metal (i.e., zero valent) forms of Group VIII metals (i.e., Pt, Pd, Ir, Rh, Os, Ru, Ni, Co and Fe), Group IVA metals (i.e., Sn and Pb), Group VB metals (i.e., Sb and Bi), and Group VIIB metals (i.e., Mn, Tc and Re). Noble metals (i.e., Pt, Pd, Ir, Rh, Os and Ru) are preferred hydrogenation/dehydrogenation components. Combinations of catalytic forms of such noble or non-noble metal, such as combinations of Pt with Sn, may be used. The valence state of the metal is preferably in a reduced valence state, e.g., when this component is in the form of an oxide or hydroxide. The reduced valence state of this metal may be attained, in situ, during the course of a reaction, when a reducing agent, such as hydrogen, is included in the feed to the reaction.

The hydrogenation/dehydrogenation component may be incorporated into the catalyst by methods known in the art, such as ion exchange, impregnation or physical admixture. For example, solutions of appropriate metal salts may be contacted with the remaining catalyst components, either before or after selectivation of the catalyst, under conditions sufficient to combine the respective components. The metal containing salt is preferably water soluble. Examples of such salts include chloroplatinic acid, tetrammineplatinum complexes, platinum chloride, tin sulfate and tin chloride.

The amount of hydrogenation/dehydrogenation component may be that amount which imparts or increases the catalytic ability of the overall catalyst to catalytically hydrogenate or dehydrogenate an organic compound under sufficient hydrogenation or dehydrogenation conditions. This amount is referred to herein as a catalytic amount. Quantitatively speaking, the present catalyst may comprise, for example, from about 0.001 to about 5 wt %, e.g., from about 0.1 to about 2 wt %, of the hydrogenation/dehydrogenation component, especially when this component is a noble metal.

When the present catalyst is used in a toluene disproportionation reaction, the inclusion of a noble metal, such as platinum, in the catalyst can serve to reduce the generation of the unwanted by-product, ethylbenzene.

EXAMPLE 1

21 grams of silica-bound HZSM-5 (HZSM-5/SiO$_2$) was heated to 900° F. in flowing hydrogen at 270 psig. The catalyst was contacted with a hydrocarbon feed mixture of 10% HMDS (hexamethyldi-siloxane)/90% toluene at 3 WHSV and a H$_2$:hydrocarbon molar ratio of 1 for 95 hours. Table 1 shows para-xylene selectivity increased from 24% for the untreated catalyst to 89% as a result of the accumulating carbido-siloxyl coating on the catalyst surface.

TABLE 1

| Time on Stream, hrs. | Toluene Conversion | p-xylene in xylenes, wt. % |
|---|---|---|
| 2 | 55 | 24 |
| 6 | 56 | 27 |
| 24 | 55 | 37 |
| 49 | 48 | 59 |
| 73 | 44 | 79 |
| 95 | 42 | 89 |

EXAMPLE 2

19.5 grams of HZSM-5/SiO$_2$ was heated to 900° F. in flowing hydrogen at 270 psig. The catalyst was contacted with a hydrocarbon feed mixture of 10% DMTS (decamethyltetrasiloxane)/90% toluene at 3 WHSV and a H$_2$:hydrocarbon molar ratio of 1 for 69 hours. Table 2 shows para-xylene selectivity increased from 23% for the untreated catalyst to 83% as a result of the accumulating carbido-siloxyl coating on the catalyst surface.

TABLE 2

| Time on Stream, hrs. | Toluene Conversion | p-xylene in xylenes, wt. % |
|---|---|---|
| 1 | 63 | 23 |
| 8 | 54 | 34 |
| 24 | 48 | 55 |
| 36 | 45 | 66 |
| 48 | 43 | 75 |
| 69 | 40 | 83 |

EXAMPLE 3

2.0 grams of HZSM-5/SiO$_2$ was heated to 900° F. in flowing hydrogen at 270 psig. The catalyst was contacted with a hydrocarbon feed mixture of 10% OMCTS (octamethylcyclotetrasiloxane)/90% toluene at 3 WHSV and a H$_2$:hydrocarbon molar ratio of 1 for 96 hours. Table 3 shows para-xylene selectivity increased from 26% for the untreated catalyst to 63% as a result of the accumulating carbidosiloxyl coating on the catalyst surface.

TABLE 3

| Time on Stream, hrs. | Toluene Conversion | p-xylene in xylenes, wt. % |
|---|---|---|
| 3 | 62 | 26 |
| 10 | 58 | 27 |
| 24 | 54 | 33 |
| 48 | 48 | 41 |
| 72 | 41 | 52 |
| 96 | 36 | 63 |

EXAMPLE 4

Selectivation of 2.0 grams of HZSM-5/SiO$_2$ was carried out at 900° F., 500 psig, 4 WHSV, and a H$_2$:hydrocarbon molar ratio of 2 using 1% phenylmethylsilicone polymer (phenyl/methyl:dimethyl ratio=1.3:1) in toluene feed. Table 4 illustrates the increase in para-xylene selectivity to 89% at 25% conversion as a result of the accumulating carbidosiloxyl coating on the catalyst surface.

TABLE 4

| Time on Stream, hrs. | Toluene Conversion | p-xylene in xylenes, wt. % |
|---|---|---|
| 1 | 56 | 22 |
| 6 | 57 | 21 |
| 22 | 51 | 24 |
| 46 | 42 | 39 |
| 98 | 36 | 70 |
| 143 | 28 | 86 |
| 170 | 25 | 89 |

EXAMPLE 5

Selectivation of 2.0 grams of HZSM-5/SiO$_2$ was carried out at 900° F., 500 psig, 4 WHSV, and a H$_2$:hydrocarbon molar ratio of 2 using 10% DMCPDS (decamethylcyclopentadisiloxane) in toluene feed. Table 5 illustrates no increase in para-xylene selectivity for this selectivating agent.

TABLE 5

| Time on Stream, hrs. | Toluene Conversion | p-xylene in xylenes, wt. % |
|---|---|---|
| 3 | 60 | 24 |
| 13 | 55 | 24 |
| 21 | 52 | 25 |

EXAMPLE 6

2.0 grams of HZSM-5/SiO$_2$ was heated to 900° F. in flowing hydrogen at 270 psig. The catalyst was contacted with a hydrocarbon feed mixture of 10% DPTMDS (diphenyltetramethyldisiloxane)/90% toluene at 3 WHSV and a H$_2$:hydrocarbon molar ratio of 1 for 2 days. Table 6 shows para-xylene selectivity increased from 24% for the untreated catalyst to 31% as a result of the accumulating carbidosiloxyl coating on the catalyst surface.

TABLE 6

| Time on Stream, hrs. | Toluene Conversion | p-xylene in xylenes, wt. % |
|---|---|---|
| 2 | 59 | 26 |
| 8 | 55 | 30 |
| 14 | 56 | 32 |
| 24 | 53 | 32 |
| 48 | 52 | 31 |

EXAMPLE 7

Selectivation of 2.0 grams of HZSM-5 was carried out at 482° C., 300 psig, 3 WHSV, and hydrogen/hydrocarbon=1 using 2% hexamethyldisiloxane in toluene feed. Table 7 illustrates the increase in para-xylene selectivity to 83% at 35% conversion as a result of the accumulating carbidosiloxyl coating on the catalyst surface.

TABLE 7

| Time on Stream, hrs. | Toluene Conversion | p-xylene in xylenes, wt. % |
|---|---|---|
| 3 | 59 | 24 |
| 71 | 41 | 65 |
| 139 | 35 | 83 |

EXAMPLE 8

Selectivation of 2.0 grams of HZSM-5 was carried out at 482° C., 300 psig, 3 WHSV, and hydrogen/hydrocarbon=2 using 2% hexamethyldisiloxane in toluene feed. Table 8 illustrates the increase in para-xylene selectivity to 88% at 38% conversion as a result of the accumulating carbidosiloxyl coating on the catalyst surface.

TABLE 8

| Time on Stream, hrs. | Toluene Conversion | p-xylene in xylenes, wt. % |
|---|---|---|
| 3 | 63 | 24 |
| 41 | 46 | 52 |
| 61 | 41 | 75 |
| 89 | 38 | 88 |

EXAMPLE 9

Selectivation of 2 0 grams of HZSM-5 was carried out at 482° C., 300 psig, 3 WHSV, and hydrogen/hydrocarbon=4 using 2% hexamethyldisiloxane in toluene feed. Table 9 illustrates the increase in para-xylene selectivity to 95% at 32% conversion as a result of the accumulating carbidosiloxyl coating on the catalyst surface.

TABLE 9

| Time on Stream, hrs. | Toluene Conversion | p-xylene in xylenes, wt. % |
|---|---|---|
| 2 | 64 | 24 |
| 48 | 37 | 79 |
| 96 | 32 | 95 |

EXAMPLE 10

Selectivation of 2.0 grams of HZSM-5 was carried out at 482° C., 300 psig, 3 WHSV, and hydrogen/hydrocarbon=6 using 2% hexamethyldisiloxane in toluene feed. Table 10 illustrates the increase in para-xylene selectivity to 81% at 35% conversion as a result of the accumulating carbido-siloxyl coating on the catalyst surface.

TABLE 10

| Time on Stream, hrs. | Toluene Conversion | p-xylene in xylenes, wt. % |
| --- | --- | --- |
| 1 | 67 | 24 |
| 25 | 45 | 40 |
| 50 | 35 | 81 |

EXAMPLE 11

Selectivation of 2.0 grams of HZSM-5 was carried out at 482° C., 300 psig, 3 WHSV, and hydrogen/hydrocarbon=1 using 2% decamethyltetrasiloxane in toluene feed. Table 11 illustrates the increase in para-xylene selectivity to 54% at 35% conversion as a result of the accumulating carbido-siloxyl coating on the catalyst surface.

TABLE 11

| Time on Stream, hrs. | Toluene Conversion | p-xylene in xylenes, wt. % |
| --- | --- | --- |
| 3 | 58 | 25 |
| 34 | 47 | 37 |
| 66 | 35 | 54 |

EXAMPLE 12

Selectivation of 2.0 grams of HZSM-5 was carried out at 482° C., 300 psig, 3 WHSV, and hydrogen/hydrocarbon=4 using 2% decamethyltetrasiloxane in toluene feed. Table 12 illustrates the increase in para-xylene selectivity to 87% at 16% conversion as a result of the accumulating carbido-siloxyl coating on the catalyst surface.

TABLE 12

| Time on Stream, hrs. | Toluene Conversion | p-xylene in xylenes, wt. % |
| --- | --- | --- |
| 1 | 63 | 24 |
| 46 | 30 | 63 |
| 94 | 16 | 87 |

EXAMPLE 13

Selectivation of 2.0 grams of HZSM-5 was carried out at 482° C., 300 psig, 3 WHSV, and hydrogen/hydrocarbon=1 using 10% decamethyltetrasiloxane in toluene feed. Table 13 illustrates the increase in para-xylene selectivity to 93% at 36% conversion as a result of the accumulating carbido-siloxyl coating on the catalyst surface.

TABLE 13

| Time on Stream, hrs. | Toluene Conversion | p-xylene in xylenes, wt. % |
| --- | --- | --- |
| 3 | 58 | 24 |
| 70 | 42 | 79 |
| 140 | 36 | 93 |

EXAMPLE 14

22.25 grams of HZSM-5/SiO$_2$ was heated to 900° F. in flowing hydrogen at 270 psig. After 1 hour, the catalyst was contacted with a hydrocarbon feed mixture of 10% DMTS (decamethyltetrasiloxane)/90% toluene at 3 WHSV and a H$_2$:hydrocarbon molar ratio of 1 for 75 hours. Table 14 shows para-xylene selectivity increased from 24% for the untreated catalyst to 87% as a result of the accumulating carbido-siloxyl coating on the catalyst surface.

TABLE 14

| Time on Stream, hrs. | Toluene Conversion | p-xylene in xylenes, wt. % |
| --- | --- | --- |
| 2 | 60 | 24 |
| 9 | 58 | 30 |
| 15 | 56 | 37 |
| 24 | 52 | 47 |
| 48 | 47 | 52 |
| 75 | 44 | 87 |

Analysis of the zeolite will indicate the presence of hydrocarbyl groups incorporated onto the zeolite from the organosilicon selectivating agent. When the functionalized zeolite is used as a catalyst in an organic conversion process, these hydrocarbyl groups may remain intact on the zeolite. More particularly, it is preferred to intentionally avoid the customary practice of precalcining the zeolite, prior to the organic conversion process, under conditions sufficient to decompose and/or burn off organic residue on the catalyst. Such precalcination conditions to be avoided may include contact of the zeolite at temperatures greater than 300° C. in an oxygen-containing atmosphere, e.g., air.

Selectivation of the zeolite may occur, in-situ, during the course of an organic conversion reaction catalyzed by the zeolite, by including an organosilicon selectivating agent, optionally along with H$_2$, in the feed to the organic conversion reaction. This type of in-situ selectivation is also referred to herein as trim selectivation.

EXAMPLE 15

22.25 grams of HZSM-5/SiO$_2$ was heated to 900° F. in flowing hydrogen at 270 psig. After 18 hours, the catalyst was contacted with a hydrocarbon feed mixture of 10% DMTS (decamethyltetrasiloxane)/90% toluene at 3 WHSV and a H$_2$:hydrocarbon molar ratio of 1 for 166 hours. Table 15 shows para-xylene selectivity increased from 24% for the untreated catalyst to 86% as a result of the accumulating carbido-siloxyl coating on the catalyst surface.

TABLE 15

| Time on Stream, hrs. | Toluene Conversion | p-xylene in xylenes, wt. % |
| --- | --- | --- |
| 2 | 71 | 24 |
| 6 | 60 | 25 |
| 24 | 55 | 32 |
| 49 | 50 | 53 |
| 96 | 46 | 74 |
| 140 | 42 | 83 |
| 166 | 40 | 86 |

EXAMPLE 16

20.0 grams of HZSM-5/SiO$_2$ was heated to 900° F. in flowing hydrogen at 270 psig. After 66 hours, the catalyst was contacted with a hydrocarbon feed mixture of 10%

DMTS (decamethyltetrasiloxane)/90% toluene at 3 WHSV and a H$_2$:hydrocarbon molar ratio of 1 for 72 hours. Table 16 shows para-xylene selectivity increased from 24% for the untreated catalyst to 69% as a result of the accumulating carbido-siloxyl siloxyl coating on the catalyst surface.

TABLE 16

| Time on Stream, hrs. | Toluene Conversion | p-xylene in xylenes, wt. % |
|---|---|---|
| 2 | 62 | 24 |
| 9 | 59 | 26 |
| 23 | 54 | 35 |
| 47 | 50 | 52 |
| 72 | 45 | 69 |

EXAMPLE 17

2.0 grams of HZSM-5/SiO$_2$ was heated to 835° F. in flowing hydrogen at 270 psig. The catalyst was contacted with a hydrocarbon feed mixture of 10% DMTS (decamethyltetrasiloxane)/90% toluene at 1.5 WHSV and a H$_2$:hydrocarbon molar ratio of 1 for 96 hours. Table 17 shows para-xylene selectivity increased from 24% for the untreated catalyst to 83% as a result of the accumulating carbido-siloxyl coating on the catalyst surface.

TABLE 17

| Time on Stream, hrs. | Toluene Conversion | p-xylene in xylenes, wt. % |
|---|---|---|
| 2 | 60 | 26 |
| 6 | 58 | 26 |
| 23 | 51 | 33 |
| 48 | 45 | 53 |
| 96 | 37 | 83 |

EXAMPLE 18

2.0 grams of HZSM-5/SiO$_2$ was heated to 900° F. in flowing hydrogen at 270 psig. The catalyst was contacted with a hydrocarbon feed mixture of 10% DMTS (decamethyltetrasiloxane)/90% toluene at 3 WHSV and a H$_2$:hydrocarbon molar ratio of 1 for 77 hours. Table 18 shows para-xylene selectivity increased from 24% for the untreated catalyst to 91% as a result of the accumulating carbido-siloxyl coating on the catalyst surface.

TABLE 18

| Time on Stream, hrs. | Toluene Conversion | p-xylene in xylenes, wt. % |
|---|---|---|
| 1 | 57 | 26 |
| 8 | 55 | 31 |
| 23 | 49 | 51 |
| 48 | 43 | 77 |
| 77 | 40 | 91 |

EXAMPLE 19

The selectivated catalyst from Example 18 was regenerated in air at 1000° F. for 6 hours. The regenerated catalyst was contacted with 100% toluene at 3 WHSV, 270 psig, and 1 H$_2$:hydrocarbon. Table 19 shows para-xylene selectivity increased from 75% for the regenerated catalyst to 89% as a result of the accumulating carbido-siloxyl coating on the catalyst surface.

TABLE 19

| Time on Stream, hrs. | Temp. °F. | Conversion wt. | p-xylene in xylenes, wt. % |
|---|---|---|---|
| 5 | 761 | 32 | 88 |
| 9 | 761 | 30 | 89 |
| 11 | 761 | 30 | 89 |

EXAMPLE 20

The regenerated catalyst from Example 19 was heated to 900° F. in hydrogen at 270 psig and contacted with a feed mixture of 10% DMTS (decamethyltetrasiloxane)/90% toluene at 3 WHSV and a H$_2$:hydrocarbon molar ratio of 1 for an additional 6 hours. Table 20 shows para-xylene selectivity increased from 75% for the regenerated catalyst to 87% as a result of the accumulating carbido-siloxyl coating on the catalyst surface. After switching to 100% toluene feed, catalyst temperature was adjusted to 788° F. to achieve 30% toluene conversion.

TABLE 20

| Time on Stream, hrs. | Toluene Conversion | p-xylene in xylenes, wt. % |
|---|---|---|
| 90% toluene | | |
| 1 (900° F.) | 46 | 75 |
| 3 | 43 | 84 |
| 5 | 42 | 87 |
| 100% toluene | | |
| 24 (788° F.) | 30 | 94 |
| 48 | 30 | 96 |
| 74 | 30 | 96 |
| 98 | 30 | 96 |

EXAMPLE 21

Selectivation of 2.0 grams of HZSM-5 was carried out at 480° C., 500 psig, 4 WHSV, and hydrogen/hydrocarbon=2 using 1% phenylmethylsilicone in toluene feed. Table 21 summarizes the toluene conversion and para-xylene selectivity as a function of time on stream.

TABLE 21

| Time on Stream, hrs. | Toluene Conversion | p-xylene in xylenes, wt. % |
|---|---|---|
| 1 | 56 | 22 |
| 22 | 51 | 24 |
| 46 | 43 | 39 |
| 70 | 39 | 55 |
| 98 | 37 | 69 |
| 120 | 31 | 81 |
| 143 | 27 | 86 |
| 190 | 25 | 91 |
| 214 | 25 | 91 |

EXAMPLE 22

Selectivation of 2.0 grams of HZSM-5 was carried out at 480° C., 500 psig, 4 WHSV, and nitrogen/hydrocarbon=2 using 1% phenylmethylsilicone in toluene feed. The conditions for this selectivation are the same as those in Example 21 above except that hydrogen has been replaced by nitrogen. Table 22 summarizes the toluene conversion and para-xylene selectivity as a function of time on stream and illustrates the criticality of hydrogen. In the absence of hydrogen rapid catalyst deactivation occurs leading to near 0% conversion. In the presence of hydrogen, however, a stable catalyst is obtained producing constant 91% para-xylene at 25% conversion. Thus, hydrogen is required for the production of a stable carbido-siloxyl coating on the catalyst surface.

TABLE 22

| Time on Stream, hrs. | Toluene Conversion | p-xylene in xylenes, wt. % |
|---|---|---|
| 1 | 54 | 23 |
| 3 | 53 | 23 |
| 5 | 49 | 23 |
| 9 | 13 | 25 |
| 12 | 4 | 34 |
| 19 | 1 | 60 |
| 25 | 0.5 | 66 |

EXAMPLE 23

A silica-modified HZSM-5 was prepared by adding 5.0 grams HZSM-5 to 1.26 grams phenylmethylsilicone dissolved in 40 cc hexane. The solvent was distilled and the catalyst was air calcined at 1° C./min. to 538° C., then 6 hours at 538° C. The catalyst contained 8% added silica.

EXAMPLE 24

Selectivation of 2.0 grams 8% $SiO_2$-HZSM-5 was carried out at 446° C., 500 psig, 4 WHSV, and hydrogen/hydrocarbon=2 using 1% phenylmethylsilicone in toluene feed. Table 23 illustrates the increase in para-xylene selectivity to 98% at 23% conversion as a result of the accumulating carbido-siloxyl coating on the catalyst surface.

TABLE 23

| Time on Stream, hrs. | Toluene Conversion | p-xylene in xylenes, wt. % |
|---|---|---|
| 2 | 34 | 30 |
| 5 | 32 | 43 |
| 7 | 30 | 67 |
| 10 | 28 | 82 |
| 13 | 25 | 96 |
| 17 | 23 | 98 |

EXAMPLE 25

A silica-modified HZSM-5 was prepared by adding 2.5 grams HZSM-5 to 0.97 grams of an emulsion of phenylmethylsilicone (0.63 gram) in water (0.31 gram). The water was distilled and catalyst was air calcined at 1° C./min. to 538° C., then 6 hours at 538° C. The catalyst contained 10% added silica.

EXAMPLE 26

Selectivation of 2.0 grams 10% $SiO_2$-HZSM-5 was carried out at 446° C., 500 psig, 4 WHSV, and hydrogen/hydrocarbon=2 using 2% hexamethyldisiloxane in toluene feed. Table 24 summarizes the increase in para-xylene selectivity to 99% at 18% conversion as a result of the accumulating carbido-siloxyl coating on the catalyst surface.

TABLE 24

| Time on Stream, hrs. | Toluene Conversion | p-xylene in xylenes, wt. % |
|---|---|---|
| 1 | 47 | 28 |
| 3 | 39 | 73 |
| 14 | 33 | 95 |
| 24 | 28 | 98 |
| 48 | 19 | 99 |

EXAMPLE 27

Selectivation of 2.0 grams 10% $SiO_2$-HZSM-5 was carried out at 446° C., 500 psig, 4 WHSV, and hydrogen/hydrocarbon=2 using 1% decamethyltetrasiloxane in toluene feed. Table 25 summarizes the increase in para-xylene selectivity to 99% at 19% conversion as a result of the accumulating carbido-siloxyl coating on the catalyst surface.

TABLE 25

| Time on Stream, hrs. | Toluene Conversion | p-xylene in xylenes, wt. % |
|---|---|---|
| 1 | 33 | 76 |
| 3 | 32 | 89 |
| 13 | 27 | 97 |
| 24 | 24 | 98 |
| 46 | 19 | 99 |

EXAMPLE 28

Selectivation of 2.0 grams 8% $SiO_2$-HZSM-5 was carried out at 483° C., 500 psig, 4 WHSV, and hydrogen/hydrocarbon=2 using 4 decamethyltetrasiloxane in toluene feed. Table 26 summarizes the increase in para-xylene selectivity to 91% at 38% conversion as a result of the accumulating carbido-siloxyl coating on the catalyst surface.

TABLE 26

| Time on Stream, hrs. | Toluene Conversion | p-xylene in xylenes, wt. % |
|---|---|---|
| 1 | 53 | 27 |
| 3 | 47 | 48 |
| 14 | 44 | 64 |
| 24 | 41 | 78 |
| 49 | 38 | 91 |

EXAMPLE 29

Selectivation of 2.0 grams 10% $SiO_2$-HZSM-5 was carried out at 446° C., 500 psig, 4 WHSV, and hydrogen/hydrocarbon=2 using 1% tetraethylorthosilicate in toluene feed. Table 27 shows that the tetraethylorthosilicate feed caused rapid catalyst deactivation and was ineffective in producing a useful carbido-siloxyl coating on the catalyst surface.

TABLE 27

| Time on Stream, hrs. | Toluene Conversion | p-xylene in xylenes, wt. % |
|---|---|---|
| 1 | 37 | 26 |
| 5 | 26 | 28 |
| 7 | 19 | 29 |
| 15 | 4 | 30 |

The following Examples demonstrate the in-situ selectivation of a pure and ex-situ selectivated zeolite powder.

In all of the aromatics processing catalytic evaluations below, the following procedure was used. 2.0 grams of the zeolite, sized to 20–40 mesh, was charged to a ⅜" o.d. micro-reactor and brought to desired unit conditions. Toluene feeds used were purified by percolating over activated alumina. Products were sampled on-line and analyzed by GC.

EXAMPLE 30

Toluene disproportionation with trim selectivation was carried out in a fixed-bed reactor using 2 grams of a silica bound HZSM-5 catalyst having a silica/alumina ratio of 26, a crystal size of 0.1 micron, an Alpha Value of 731, and 1% silicone compound having a phenylmethyl silicon to dimethyl silicon ratio of 1:1 in a toluene feed. Operating conditions were 4.0 WHSV, 480° C., 500 psig, and a hydrogen/hydrocarbon ratio of 2. Table 28 summarizes toluene conversion and para-xylene selectivity as a function of time on stream during and after trim selectivation.

TABLE 28

| Time on Stream, hrs. | Toluene Conversion | p-xylene in xylenes, wt. % |
|---|---|---|
| 1 | 56 | 22 |
| 6 | 57 | 21 |
| 22 | 51 | 24 |
| 46 | 42 | 39 |
| 98 | 36 | 70 |
| 143 | 28 | 86 |
| 170 | 25 | 89 |
| 174* | 25 | 91 |
| 342* | 25 | 91 |

It is noteworthy that the silicone trim selectivation substantially increased para-xylene selectivity from an initial 22% to 89%. At 174 hours on stream the feed was changed to 100% toluene, i.e., the silicone co-feed was discontinued. Over the following one week test period, toluene conversion remained constant at 25% and para-xylene selectivity remained constant at 91%.

EXAMPLE 31

Toluene disproportionation with trim selectivation of 2 grams of silica bound HZSM-5 was carried out at 4.0 WHSV, 446° C., 500 psig, and a hydrogen/hydrocarbon ratio=2. Table 29 summarizes toluene conversion and para-xylene selectivity as a function of time on stream.

TABLE 29

| Time on Stream, hrs. | Toluene Conversion | p-xylene in xylenes, wt. % |
|---|---|---|
| 1 | 44 | 29 |
| 25 | 42 | 34 |
| 47 | 37 | 58 |
| 94 | 31 | 86 |
| 143 | 29 | 93 |
| 176 | 27 | 96 |
| 199 | 26 | 97 |
| 223 | 25 | 97 |
| 239* | 25 | 97 |

*Silicone co-feed discontinued.

Silicone selectivation increased para-xylene selectivity from 24% (thermodynamic value) to a high 97% at 25% toluene conversion. When the silicone co-feed was discontinued, the para-xylene selectivity and toluene conversion were unchanged at 97% and 25%, respectively.

EXAMPLE 32

Toluene disproportionation with trim selectivation of 2 g of a silica bound HZSM-5 was also carried out at 4.0 WHSV, 420° C., 0 psig, and hydrogen/hydrocarbon ratio=0. Table 30 summarizes toluene conversion and para-xylene selectivity as a function of time on stream. Note that the conversion drops to essentially zero at 184 hours on stream in contrast to operation in the presence of hydrogen where at 184 hours on stream conversion has stabilized at 25%.

TABLE 30

| Time on Stream, hr | Conversion, wt % | para-Xylene in Xylenes, wt % |
|---|---|---|
| 1 | 14 | 27 |
| 48 | 8 | 51 |
| 96 | 2 | 82 |
| 136 | 1 | 93 |
| 184 | 0.1 | 97 |

During this reaction, a toluene feedstock comprising 1% phenylmethyl silicone and hydrogen or nitrogen in an amount equal to a subject gas to hydrocarbon ratio of 2, was fed over the catalyst at 480° C., at a pressure of 500 PSIG and at WHSV of 4. The para-selectivity of the reaction in the presence of hydrogen gas increased steadily to a level of about 90% at a toluene-to-xylene conversion of about 25%. As indicated in Table 28, the para-selectivity and conversion continued at high levels even after the feedstock was changed to 100% toluene after about 170 hours on stream. In the presence of nitrogen, on the other hand, the catalyst deactivated rapidly and conversion quickly approached zero. The results of Table 28 therefore indicate that the use of nitrogen with toluene and a silicone selectivating agent in the absence of hydrogen fails to provide the advantages of the present invention.

The spent catalyst can be regenerated by methods known in the art, such as by air regeneration. Thereafter, the catalyst can once again be trim selectivated and reused.

EXAMPLE 33

Toluene disproportionation with trim selectivation of $SiO_2$-HZSM-5 was carried out using 1% octamethylcyclotetrasiloxane in toluene feed. Operating conditions were 446° C., 500 psig, 4.0 WHSV, and $H_2$/HC=2. Table 31 summarizes the results.

TABLE 31

| Time on Stream, hrs. | p-Xylene/Xylenes, wt % | Toluene Conversion, wt % |
|---|---|---|
| 0 | 25 | 40 |
| 24 | 88 | 23 |
| 46 | 95 | 18 |
| 71 | 98 | 15 |

EXAMPLE 34

Toluene disproportionation with trim selectivation as in Example 33 was carried out using hexamethyldisiloxane. Table 32 summarizes the results.

TABLE 32

| Time on Stream, hrs. | p-Xylene in Xylenes, wt % | Toluene Conversion, wt % |
|---|---|---|
| 1 | 28 | 47 |
| 2 | 56 | 42 |
| 4 | 80 | 37 |
| 14 | 95 | 33 |
| 24 | 98 | 28 |
| 47 | 99 | 20 |
| 54 | 99 | 18 |

The high p-xylene selectivity and toluene conversion continued over 350 hours on stream. The toluene conversion remained at about 18–20% with a p-xylene selectivity of 99% for an extended period of time. HMDS was discontinued at about 50 hours.

EXAMPLES 35–42

Toluene disproportionations with trim selectivations as in Examples 33 and 34 were carried out with the siloxanes listed in Table 33. Operating conditions were 446° C., 500 psig, 4.0 WHSV and $H_2/HC=2$. The results after 24 hours are shown in Table 33.

TABLE 33

| Ex. | Siloxanes | p-Xylene/ Xylenes, wt. % | Toluene Conversion wt. % |
|---|---|---|---|
| 35 | Hexamethylcyclotrisiloxane | 84[a] | 20 |
| 36 | 1,3,5-Trimethyl-1,3,5-triphenylcyclotrisiloxane | 85 | 31 |
| 37 | Octamethylcyclotetrasiloxane | 88 | 23 |
| 38 | Decamethylcyclopentasiloxane | 90 | 28 |
| 39 | Decamethyltetrasiloxane | 98 | 24 |
| 40 | Hexamethyldisiloxane | 98 | 24 |
| 41 | 1,1,3,3,5,5-Hexamethyltrisiloxane | 96 | 14 |
| 42 | Octamethyltrisiloxane | 81 | 20 |

[a] 41 hours on stream

EXAMPLES 43–47

For comparison purposes, the compounds listed in Table 34 were tested as in Examples 35–42 with results shown in Table 34.

TABLE 34

| Ex. | Siloxanes | p-Xylene/ Xylenes, wt. % | Toluene Conversion wt. % |
|---|---|---|---|
| 43 | Hexaphenylcyclotrisiloxane | 43 | 29 |
| 44 | Octaphenylcyclotetrasiloxane | 66 | 28 |
| 45 | Tetra-(n-butyl)-orthosilicate | 36 | 2 |
| 46 | Tetra-ethyl-orthosilicate | 38 | 3 |
| 47 | Tetra-(2-ethylhexyl)-orthosilicate | 33 | 1 |

EXAMPLE 48

Toluene alkylation with ethylene was carried out at 468° C. and 100 psig over 1.0 g $SiO_2$-HZSM-5 catalyst trim selectivated using 1% phenylmethyl silicone in toluene at 446° C., 500 psig, WHSV, and $H_2/HC=2$. Toluene was pumped at 4 WHSV. Ethylene and hydrogen were cofed to maintain the mole ratio toluene/ethylene/hydrogen=8/1/3. At 10% toluene conversion (80% of the 12.5% theoretical maximum conversion), the selectivity to p-ethyltoluene was a very high 99.1% with only 0.9% m-ethyltoluene.

EXAMPLE 49

Toluene alkylation with methanol was carried out at 448° C. and 500 psig over 2.00 g $SiO_2$-HZSM-5 catalyst trim selectivated as described above. Toluene was pumped at 4 WHSV. Methanol and hydrogen were cofed to maintain the mole ratio toluene/methanol/hydrogen=4/1/8. At 14% toluene conversion (56% of the theoretical 25% maximum conversion), the selectivity to p-xylene was a very high 99.9% with only 0.1% m-xylene.

EXAMPLE 50

Conversion of n-heptane was carried out 446° C., 0 psig, and 4 WHSV over 2.00 g $SiO_2$-HZSM-5 catalyst trim selectivated as described above. The aromatic product distribution at 21% heptane conversion is shown in the following table. The p-xylene selectivity in the xylene fraction was a very high 99.3% with only 0.7% m-xylene.

| Component | Wt. % |
|---|---|
| Benzene | 6.2 |
| Toluene | 44.6 |
| Ethylbenzene | 4.7 |
| Xylenes | 39.5 |
| p-Ethyltoluene | 5.0 |
| | 100.0 |

EXAMPLE 51

Conversion of methanol was carried out at 371° C., 0 psig, and 1 WHSV over 1.00 g $SiO_2$-HZSM-5 catalyst trim selectivated as described above. The liquid product distribution at 100% methanol conversion is shown in the following table

| Component | Wt. % |
|---|---|
| $C_5$–$C_6$ | 2.0 |
| Benzene | 7.3 |
| Toluene | 84.0 |
| Ethylbenzene | 2.2 |
| Xylenes | 42.1 |
| $C_{9+}$ | 12.4 |
| | 100.0 |

EXAMPLE 52

A Fries reaction of phenylacetate is carried out at 400° C., 100 psig, and 1 WHSV over $SiO_2$-HZSM-5 catalyst trim selectivated as described above. The 4-hydroxyaceto-phenone product is obtained in high selectivity. EXAMPLE 53

Propylene oligomerization is carried out at 200° C., 600 psig, and 0.25 WHSV over $SiO_2$-HZSM-5 catalyst trim selectivated as described above. The diesel and lube products are obtained with high selectivity to the desirable straight chain hydrocarbons.

EXAMPLE 54

Distillate dewaxing is carried out at 650° F., 400 psig, and 1 WHSV over $SiO_2$-HZSM-5 catalyst trim selectivated as described above. The product quality is substantially improved by the selective cracking of straight chain, waxy hydrocarbons. The pour point of a heavy gas oil improves from 95° F. to 20° F. while the cloud point improves from 96° F. to 20° F.

EXAMPLE 55

A silica modified HZSM-5 was prepared by adding 5.00 g HZSM-5 to 1.26 g phenylmethylpolysiloxane dissolved in 40 cc hexane. The solvent was distilled and the catalyst was air calcined at 1° C./min to 538° C., then 6 hours at 538° C. The catalyst contained a nominal 10% added silica.

Silicone trim selectivation of the 10% $SiO_2$-HZSM-5 was carried out at 446° C., 500 psig, 4.0 WHSV, and hydrogen/hydrocarbon ratio=2. Table 35 shows toluene conversion and para-xylene selectivity for 10% $SiO_2$-HZSM-5 as a function of time on stream.

TABLE 35

Silicone Selectivation of 10% $SiO_2$-HZSM-5

| Time on Stream, hrs | Toluene Conversion, wt % | Para-xylene in Xylenes, wt % |
|---|---|---|
| 2 | 25 | 33 |
| 4 | 24 | 43 |
| 6 | 23 | 72 |
| 8 | 21 | 84 |
| 10 | 21 | 89 |
| 15 | 19 | 94 |
| 20 | 18 | 96 |
| 28 | 18 | 98 |

The silicone trim selectivation substantially increased para-xylene selectivity from 33% to 98% over 28 hours on stream. Feed was then changed to 100% toluene. Over the next ten hours the selectivity increased to 99% at 16% conversion. To further increase conversion, the temperature was increased to 457° C. and shortly thereafter to 468° C. The conversion rose to 21%, then decreased slightly to 20% over the next 80 hours. The para-xylene selectivity increased from 99.2% to 99.6% over the same 80 hours.

Compared to the HZSM-5 at Example 30, the 10% $SiO_2$-HZSM-5 catalyst showed a substantially higher selectivation rate. For silica-modified HZSM-5, 89% para-xylene selectivity was achieved after only 10 hours on stream (17 times faster than the 170 hours for the HZSM-5 parent). Also, the time needed to reach optimum para-selectivation, 1 day for $SiO_2$-HZSM-5 compared to 1 week for HZSM-5, was shorter despite the higher selectivation temperature for HZSM-5 (480° C. vs. 446° C.).

The total phenylmethyl silicone consumption was 6.80 g silicone per g HZSM-5 and 1.42 gram of silicone per gram of $SiO_2$-HZSM-5. Thus selectivation of $SiO_2$-HZSM-5 consumed nearly five (4.79) times less silicone than selectivation of HZSM-5 and therein shows a catalyst cost advantage.

EXAMPLE 56

Silicone trim selectivation of 5% $SiO_2$-HZSM-5 was carried out at 446° C., 500 psig, 4.0WHSV, and hydrogen/hydrocarbon ratio=2. The 5% $SiO_2$ catalyst was more active than the 10% $SiO_2$ catalyst and was expected to produce a more active selectivated catalyst. Table 36 shows toluene conversion and para-xylene selectivity for 5% $SiO_2$-HZSM-5 as a function of time on stream.

TABLE 36

Silicone Selectivation of 5% $SiO_2$-HZSM-5

| Time on Stream, hrs | Toluene Conversion, wt % | Para-xylene in Xylenes, wt % |
|---|---|---|
| 2 | 41 | 25 |
| 4 | 41 | 27 |
| 5 | 38 | 36 |
| 7 | 35 | 54 |
| 14 | 31 | 83 |
| 21 | 27 | 95 |
| 26 | 25 | 98 |

Silicone selectivation substantially increased para-xylene selectivity from 25% to 98% over 26 hours on stream. Compared to 10% $SiO_2$-HZSM-5, the 5% $SiO_2$ catalyst showed consistently higher conversion over the one day selectivation time. Feed was then changed to 100% toluene. Over the next 6 hours the selectivity increased to 99% at 24% conversion, temperature was increased to 468° C. and WHSV was decreased to 3. Conversion increased to 27%, then gradually decreased to and remained constant at 21% for 6 days (146 hours). Correspondingly, the para-xylene selectivity was initially unchanged at 99% then gradually increased to and remained constant at 99.6%–99.9% for 6 days when the run was arbitrarily terminated.

EXAMPLE 57

A 0.05% Pt-10% $SiO_2$-HZSM-5 catalyst was prepared by adding 2.50 g of the 10% $SiO_2$-HZSM-5 prepared in Example 55 to 12.5 cc 1M ammonium nitrate solution. After 1.5 hours, a solution of 0.0025 g tetraamine platinum(II)nitrate in approximately 0.5 cc water was added. After standing overnight the catalyst was filtered, washed with water, and air calcined at 5° C./min to 350° C., then 3 hours at 350° C.

Toluene disproportionation was carried out over 2.00 g of the catalyst of Example 57 at 446° C., 500 psig, 4 WHSV, and a hydrogen/hydrocarbon mole ration of 2.0. Table 37 shows the product distribution compared to that of Pt-free silica-modified HZSM-5 from Example 55 tested under the same operating conditions. At similar toluene conversion, the ethylbenzene product was reduced by nearly a factor of 12 using the Pt-catalyst. The undesirable $C_9^+$ aromatics product also was reduced by nearly a factor of 2.

TABLE 37

| Component, wt % | Pt—$SiO_2$-HZSM-5 | $SiO_2$-HZSM-5 |
|---|---|---|
| Benzene | 45.84 | 41.65 |
| Ethylbenzene | 0.05 | 0.59 |
| Xylenes | 43.12 | 55.98 |
| $C_{9+}$ Aromatics | 0.99 | 1.78 |
|  | 100.00 | 100.00 |
| Ethylbenzene in $C_8$, wt. | 0.10 | 1.18 |
| p-Xylene in Xylenes, wt % | 25.8 | 29.8 |
| Toluene Conversion, wt % | 35 | 34 |

EXAMPLE 58

The catalyst of Example 57 was treated in situ with a 1% solution of phenymethylpolysiloxane in toluene at 446° C., 500 psig, 4 WHSV, and a hydrogen/hydrocarbon mole ratio of 2.0. After 32 hours on stream the feed was changed to 100% toluene. Table 38 shows the product distribution compared to that of Pt-free, siloxane treated, silica-modified HZSM-5 tested under the same operating conditions.

TABLE 38

| Component, wt % | Pt—SiO$_2$-HZSM-5 | SiO$_2$-HZSM-5 |
|---|---|---|
| Benzene | 46.62 | 38.43 |
| Ethylbenzene | 0.33 | 1.18 |
| Xylenes | 52.35 | 58.56 |
| C$_9$ + Aromatics | 0.70 | 1.83 |
|  | 100.00 | 100.00 |
| Ethylbenzene in C$_8$, wt % | 0.63 | 1.98 |
| p-Xylene in Xylenes, wt % | 98.4 | 98.7 |
| Toluene Conversion, wt % | 25 | 22 |

At similar toluene conversion, the ethylbenzene product was reduced by a factor of 3.6 using the Pt-catalyst while the p-xylene selectivities remained very high at 98.4%–98.7%. The undesirable C$_9^+$ aromatics product was also reduced by nearly a factor of 3.

The results of Examples 59, 60 and 61, which are reported in Table 39, indicate the beneficial effect on reducing ethylbenzene in the product stream by the addition of platinum to the catalytic molecular sieve.

EXAMPLE 59

Silicone selectivation of a 10% SiO$_2$-HZSM-5 was carried out using 1% phenylmethyl silicone in a toluene feed at 446° C., 500 psig, 4.0 WHSV, and a hydrogen/hydrocarbon ratio=2. At 31 hours on stream the feed was changed to 100% toluene. At 52 hours on stream the temperature was increased to 468° C. and at 165 hours the WHSV was lowered to 3.0. The data at 39 days on stream are shown in column 1 of Table 39.

EXAMPLE 60

Silicone selectivation of a 0.025% Pt 10% SiO$_2$-HZSM-5 was carried out using 1% phenylmethyl silicone in a toluene feed at 446° C., 500 psig, 4.0WHSV, and a hydrogen/hydrocarbon ratio=2. At 56 hours on stream the feed was changed to 100% toluene. At 73 hours on stream the temperature was increased to 468° C. The data at 7 days on stream are shown in column 2 of Table 39.

EXAMPLE 61

Silicone selectivation of a nitric acid activated 0.05% Pt 10% SiO$_2$-HZSM-5 was carried out using 1% phenylmethyl silicone in a toluene feed at 446° C., 500 psig, 4.0 WHSV, and a hydrogen/ hydrocarbon ratio=2. At 27 hours on stream the feed was changed to 100% toluene. Temperature, WHSV, and hydrogen/hydrocarbon ratio were varied during the run. The data at 13 days on stream are shown in column 3 of Table 39.

TABLE 39

|  | Silicone | Silicone/Pt | |
|---|---|---|---|
|  | Ex. 36 | Ex. 37 | Ex. 38 |
| Reaction Conditions |  |  |  |
| Temperature, °C. | 468 | 468 | 431 |
| Pressure, psig | 500 | 500 | 500 |
| H$_2$/HC | 2 | 2 | 8 |
| WHSV | 3 | 4 | 4 |
| Time on Stream, days | 39 | 7 | 13 |
| Toluene Conversion, wt % | 23 | 20 | 21 |

TABLE 39-continued

|  | Silicone | Silicone/Pt | |
|---|---|---|---|
|  | Ex. 36 | Ex. 37 | Ex. 38 |
| Products, wt % |  |  |  |
| C$_5^-$ | 2.5 | 2.5 | 2.5 |
| Benzene | 43.0 | 43.6 | 47.2 |
| Ethylbenzene | 1.9 | 0.2 | 0.1 |
| Xylenes | 50.4 | 53.1 | 50.0 |
| Ethyltoluenes | 1.9 | 0.5 | 0.2 |
| C$_{10}^+$ | 0.3 | 0.1 | 0.0 |
|  | 100.0 | 100.0 | 100.0 |
| p-Xylene | 99.7 | 98.7 | 99.7 |
| m-Xylene | 0.3 | 1.3 | 0.3 |
| o-Xylene | tr. | tr. | tr. |
|  | 100.0 | 100.0 | 100.0 |
| Benzene/Xylenes, m/m | 1.2 | 1.1 | 1.3 |
| p-XylenePurity, wt % | 97.8 | 98.3 | 99.5 |

Examples 59 through 61 indicate that the levels of ethylbenzene in the reaction products of the present invention can be reduced by using a catalytic molecular sieve with a hydrogenation/dehydrogenation function such as platinum incorporated into the catalytic molecular sieve. The level of ethylbenzene in the product stream is preferably at a commercially acceptable level of not greater than 0.3%, and is most preferably not greater than about 0.2%.

As stated above, the present invention advantageously provides a product stream having a high para-xylene purity with respect to the other C, products. Table 40 provides the relative proportions of para-xylene to various combinations of other products.

TABLE 40

Comparison of Product Parameters
CATALYST

| Parameter | Silicone | Silicone/Pt | | Calculated Equilibrium Value |
|---|---|---|---|---|
|  | Ex. 36 | Ex. 37 | Ex. 38 |  |
| p-Xylene/EB | 26.4 | 262 | 498 | 2.5 |
| p-Xyl/EB + m,o-xyl (other C$_8$) | 23.9 | 58.2 | 166 | 2.5 |
| p-Xyl/EB + m,o-Xyl + C$_9$ (other C$_8$ + C$_9$) | 12.63 | 37.4 | 99.6 | 1.6 |
| p-Xylene purity (in all C$_8$s), wt % | 95.7 | 98.3 | 99.5 | 71.8 |
| p-Xylene yield (based on all products and toluene), wt % | 10.6 | 10.6 | 10.2 | 11.9 |

What is claimed is:

1. A zeolite functionalized with at least one organosiliceous group of the formula, SiR$_n$(OX)$_{4-n}$, where R is at least one hydrocarbyl group, n is 1 or 2 and X is Si or H.

2. A zeolite according to claim 1, wherein R is an alkyl or aryl group having from 1 to 10 carbon atoms.

3. A zeolite according to claim 2, wherein R is a methyl or phenyl group.

4. A zeolite according to claim 1, where R is a methyl group.

5. A zeolite according to claim 1 having a silica to alumina molar ratio of at least 20.

6. A zeolite according to claim 5 having a silica to alumina molar ratio of 60 or less.

7. A zeolite according to claim 6 having a Constraint Index of from 1 to 12.

8. A zeolite according to claim 6 which is ZSM-5 functionalized with at least one group of the formula, $Si(CH_3)_2(OX)_2$, and functionalized with at least one group of the formula, $Si(CH_3)(OX)_3$, where X is Si or H.

9. A zeolite according to claim 8 having a sorption capacity for n-hexane of at least 6 wt. %.

10. A zeolite according to claim 5, wherein said organosiliceous groups are located substantially on the external surface of said zeolite.

11. A zeolite according to claim 6 which is combined with a binder material.

12. A zeolite according to claim 8 which is combined with a silica binder.

13. A zeolite according to claim 1 which has been functionalized with said organosiliceous group by contacting the zeolite with a silicone compound having at least two silicon atoms per molecule.

14. A zeolite according to claim 13, wherein said silicone compound is of the formula where $R_1$, $R_2$, $R_3$, $R_4$, $R_5$, and $R_6$ are independently methyl or phenyl and m is from 1 to 10.

15. A zeolite according to claim 14, wherein said silicone compound is selected from the group consisting of hexamethyldisiloxane, decamethyltetrasiloxane and diphenyltetramethyldisiloxane.

16. A zeolite according to claim 13, wherein said silicone compound is selected from the group consisting of octamethylcyclotetrasiloxane and decamethylcyclo-pentasiloxane.

17. A zeolite according to claim 13 which has been functionalized by contacting the zeolite with said silicone compound under vapor phase conditions in the presence of hydrogen.

18. A zeolite according to claim 17 which has been functionalized by contacting the zeolite with said silicone compound under vapor phase conditions in the presence of an organic carrier.

19. A zeolite according to claim 18, wherein said organic carrier is toluene.

20. A method for preparing a zeolite according to claim 1, said method comprising reacting said zeolite with a silicone compound under vapor phase conditions, said silicone compound having at least two silicon atoms, the silicon atoms being connected to one another through oxygen atoms, the remainder of the bonds extending from the silicon atoms being connected to hydrocarbyl groups having from 1 to 10 carbon atoms.

21. A method according to claim 20, wherein the silicon and oxygen atoms in said silicone compound form a cyclic structure.

22. A method according to claim 21, wherein said silicone compound is selected from the group consisting of octamethylcyclotetrasiloxane and decamethylcyclo-pentasiloxane.

23. A method according to claim 20, wherein said silicone compound has the formula where $R_1$, $R_2$, $R_3$, $R_4$, $R_5$, and $R_6$ are independently methyl or phenyl and m is from 1 to 10.

24. A method according to claim 23, wherein said silicone compound is selected from the group consisting of hexamethyldisiloxane, decamethyltetrasiloxane and diphenyltetramethyldisiloxane.

25. A method according to claim 20, wherein said zeolite has a silica to alumina molar ratio of at least 20.

26. A method according to claim 25, wherein said zeolite has a silica to alumina molar ratio of 60 or less.

27. A method according to claim 26, wherein said zeolite has a Constraint Index of from 1 to 12.

28. A method according to claim 20, wherein said zeolite is ZSM-5.

29. A method according to claim 26, wherein said zeolite is ZSM-5.

30. A method according to claim 20, wherein said zeolite is combined with a binder material prior to contact with said silicone compound.

31. A method according to claim 28, wherein said zeolite is combined with a silica binder material prior to contact with said silicone compound.

32. A method according to claim 29, wherein said zeolite is combined with a silica binder material prior to contact with said silicone compound.

33. A method according to claim 20, wherein said zeolite is contacted with an organosilicon compound, followed by calcination in an oxygen containing atmosphere, prior to contact of said zeolite with said silicone compound.

34. A method according to claim 20, wherein said zeolite is contacted with said silicone compound in the presence of hydrogen and an organic carrier.

35. A method according to claim 34, wherein said organic carrier is toluene.

36. A method according to claim 29, wherein said silicone compound is hexamethyldisiloxane.

37. A method according to claim 29, wherein said silicone compound is decamethyltetrasiloxane.

38. A method according to claim 29, wherein said silicone compound is diphenyltetramethyldisiloxane.

39. A method according to claim 29, wherein said silicone compound is octamethylcyclotetrasiloxane.

40. A method according to claim 29, wherein said silicone compound is decamethylcyclopentasiloxane.

* * * * *